(12) United States Patent
Bradley

(10) Patent No.: US 10,755,814 B2
(45) Date of Patent: Aug. 25, 2020

(54) METHOD AND APPARATUS FOR VERIFYING COMPLIANCE WITH DENTAL APPLIANCE THERAPY

(71) Applicant: BRAEBON MEDICAL CORPORATION, Kanata (CA)

(72) Inventor: Donald Carmon Bradley, Ottawa (CA)

(*) Notice: Subject to any disclaimer, the term of this patent is extended or adjusted under 35 U.S.C. 154(b) by 340 days.

(21) Appl. No.: 15/917,320

(22) Filed: Mar. 9, 2018

(65) Prior Publication Data

US 2018/0261324 A1 Sep. 13, 2018

Related U.S. Application Data

(60) Continuation of application No. 14/619,848, filed on Feb. 11, 2015, now abandoned, which is a division of
(Continued)

(51) Int. Cl.
| | | |
|---|---|---|
| G16H 20/40 | (2018.01) | |
| G16H 40/67 | (2018.01) | |
| A61B 5/00 | (2006.01) | |
| A61C 19/04 | (2006.01) | |
| A61F 5/56 | (2006.01) | |

(Continued)

(52) U.S. Cl.
CPC ............ *G16H 40/67* (2018.01); *A61B 5/01* (2013.01); *A61B 5/11* (2013.01); *A61B 5/4818* (2013.01); *A61B 5/4833* (2013.01); *A61B 5/682* (2013.01); *A61B 5/6847* (2013.01); *A61C 7/00* (2013.01); *A61C 19/04* (2013.01); *A61F 5/566* (2013.01); *G01B 21/22* (2013.01); *G01K 13/00* (2013.01); *G06F 19/3481* (2013.01); *A61B 5/7257* (2013.01); *A61B 2560/0209* (2013.01); *A61B 2560/0481* (2013.01); *A61B 2562/0219* (2013.01); *A61B 2562/0271* (2013.01); *G07C 3/08* (2013.01); *Y02A 90/26* (2018.01)

(58) Field of Classification Search
CPC ...................................................... G16H 20/40
USPC ............... 705/2; 702/19; 340/575; 131/329; 73/587

See application file for complete search history.

(56) References Cited

U.S. PATENT DOCUMENTS

| | | |
|---|---|---|
| 5,774,425 A | 6/1998 | Ivanov et al. |
| 5,980,246 A | 11/1999 | Ramsay et al. |
| | (Continued) | |

FOREIGN PATENT DOCUMENTS

| | | |
|---|---|---|
| AT | 409216 B | 6/2002 |
| CN | 101553194 A | 10/2009 |
| | (Continued) | |

OTHER PUBLICATIONS

Australian Patent Application No. 2017200524, Examination Report dated Apr. 25, 2018.
(Continued)

*Primary Examiner* — John A Pauls
(74) *Attorney, Agent, or Firm* — Borden Ladner Gervais LLP; Jason Mueller-Neuhaus

(57) ABSTRACT

A method and an apparatus for verifying compliance with a dental appliance therapy for a human patient is described. At least one parameter of a dental appliance worn by the human patient is periodically measured and compliance with the dental appliance therapy is determined by performing a spectral analysis of the measured parameter.

20 Claims, 13 Drawing Sheets

Related U.S. Application Data application No. 14/111,079, filed as application No. PCT/CA2012/050845 on Nov. 23, 2012, now abandoned.

(60) Provisional application No. 61/563,693, filed on Nov. 25, 2011.

(51) Int. Cl.
| | | |
|---|---|---|
| *A61C 7/00* | (2006.01) | |
| *A61B 5/01* | (2006.01) | |
| *A61B 5/11* | (2006.01) | |
| *G01B 21/22* | (2006.01) | |
| *G01K 13/00* | (2006.01) | |
| *G06F 19/00* | (2018.01) | |
| *G07C 3/08* | (2006.01) | |

(56) References Cited

U.S. PATENT DOCUMENTS

| | | |
|---|---|---|
| 6,798,718 B1 | 9/2004 | Masaki et al. |
| 6,880,967 B2 | 4/2005 | Isozumi et al. |
| 7,387,435 B2 | 6/2008 | Kishi |
| 7,480,588 B1 | 1/2009 | Walker |
| 7,535,786 B1 | 5/2009 | Walker |
| 7,553,157 B2 | 6/2009 | Abolfathi et al. |
| 7,603,249 B1 | 10/2009 | Walker |
| 2002/0124652 A1* | 9/2002 | Schultz ............... E21B 12/02 73/587 |
| 2006/0166157 A1 | 7/2006 | Rahman et al. |
| 2007/0283973 A1* | 12/2007 | Longley ............... A61F 5/566 131/329 |
| 2008/0161731 A1 | 7/2008 | Woods et al. |
| 2009/0105523 A1 | 4/2009 | Kassayan et al. |
| 2010/0152599 A1 | 6/2010 | Duhamel et al. |
| 2010/0312484 A1* | 12/2010 | DuHamel ............. A61B 5/01 702/19 |
| 2012/0169503 A1 | 7/2012 | Wu et al. |
| 2012/0240941 A1 | 9/2012 | Rosenman et al. |
| 2013/0050019 A1 | 2/2013 | Mahmoud |

FOREIGN PATENT DOCUMENTS

| | | |
|---|---|---|
| CN | 101686852 A | 3/2010 |
| JP | 2008514281 A | 5/2008 |

OTHER PUBLICATIONS

Australian Patent Application No. 2012343270, Examination Report dated May 26, 2016.
Brandl et al., "A Low-Cost Wireless Sensor System and Its Application in Dental Retainers," IEEE Sensors Journal, Mar. 2009, vol. 9 (3), pp. 255-262.
Chinese Patent Application No. 201280064487.9, Office Action dated May 27, 2015—English Translation available.
Chinese Patent Application No. CN201510920178.2, Office Action dated Sep. 28, 2017—with English Translation.
European Patent Application No. 12851517, Supplementary European Search Report dated Apr. 13, 2015.
European Patent Application No. 12851517.8, Office Action dated Feb. 12, 2016.
European Patent Application No. 17157722.4, Extended European Search Report dated Jun. 29, 2017.
International Patent Application No. PCT/CA2012/050845, International Preliminary Report on Patentability dated Jun. 5, 2014.
International Patent Application No. PCT/CA2012/050845, International Search Report dated Feb. 26, 2013.
Israeli Patent Application No. 232734, Office Action dated Oct. 18, 2017—English Translation available.
Japanese Patent Application No. 2014-542657, Office Action dated Jan. 13, 2017—English Translation available.
Japanese Patent Application No. 2014-542657, Office Action dated Jul. 21, 2017—with English Translation.
Schott et al., "Applicative Characteristics of New Microelectronic Sensors Smart Retainer and TheraMon for Measuring Wear Time," Journal of Orofacial Orthopedics, Sep. 2010, vol. 71 (5), pp. 339-347.
U.S. Appl. No. 14/111,079, Office Action dated Feb. 18, 2015.
U.S. Appl. No. 14/111,079, Office Action dated May 4, 2015.
U.S. Appl. No. 14/111,079, Office Action dated Sep. 30, 2015.
U.S. Appl. No. 14/619,848, Final Office Action dated Feb. 23, 2017.
U.S. Appl. No. 14/619,848, Final Office Action dated Nov. 17, 2015.
U.S. Appl. No. 14/619,848, Non-Final Office Action dated Sep. 13, 2016.
U.S. Appl. No. 14/619,848, Office Action dated Aug. 6, 2015.
Wikipedia Contributors, "Inclinometer," Wikipeida the free encyclopedia, [online], Oct. 14, 2011. Retrieved from the Internet:, 6 pages.
Indian Patent Application No. 912/MUMNP/2014, Office Action dated Feb. 20, 2020.

* cited by examiner

METHOD AND APPARATUS FOR VERIFYING COMPLIANCE WITH DENTAL APPLIANCE THERAPY

CROSS-REFERENCE TO RELATED APPLICATIONS

This application is a continuation of U.S. patent application Ser. No. 14/619,848 filed on Feb. 11, 2015 which is a divisional of U.S. patent application Ser. No. 14/111,079 filed on Oct. 10, 2013 which is a national phase entry of PCT/CA2012/050845 filed Nov. 23, 2012, which claims priority to U.S. Provisional Application No. 61/563,693 filed on Nov. 25, 2011, the contents of which are incorporated by reference in their entirety.

FIELD

The present invention is related to dental appliances. In particular, the present invention is related to a method and apparatus for verifying compliance with dental appliance therapy.

BACKGROUND

Sleep apnea is characterized by a cessation or reduction of breathing during sleep. Obstructive sleep apnea (OSA) refers to apnea syndromes due primarily to collapse of the upper airway during sleep. It is estimated that 2 to 4% of middle-aged North Americans suffer from obstructive sleep apnea (OSA). Left untreated, sleep apnea is known to cause or aggravate other serious medical conditions, including heart disease, hypertension, and hypoxia. However, because episodes of apnea interrupt sleep, the most noticeable consequences of the untreated condition are fatigue and daytime sleepiness. These conditions are dangerous for individuals practicing a profession requiring alertness, and particularly those professions in which the work may be monotonous. For example, it is believed that OSA has been a contributing factor in numerous traffic accidents involving long-distance truck-drivers.

One frequently prescribed course of treatment for OSA is mandibular advancement therapy. This treatment consists of mechanically positioning the lower jaw (mandible) of the patient forward, and maintaining that position for the duration of sleep. This is accomplished by fitting the patient with a dental appliance, known as a mandibular advancement device (MAD). The MAD is similar in appearance to an orthodontic retainer or a protective mouth-guard, and is manufactured by a qualified dental health care provider. The MAD is typically in two parts: an upper part fitted to the upper teeth, and a lower part fitted to the lower teeth. The relative position of the two parts determines the degree of mandibular advancement. During sleep, the two parts are attached together such that the lower mandible is not able to fall back. On some MADs the relative position is adjustable by the dental health care provider. The American Academy of Sleep Medicine has acknowledged that Mandibular advancement therapy is effective for treating mild to moderate sleep apnea. The anterior mandibular position helps prevent collapse of the soft tissue in the palate which is frequently the cause of obstructive sleep apnea, thus improving the quality of sleep, and consequently, daytime alertness.

For individuals employed in professions where a lack of alertness is a danger to public safety, treatment of obstructive sleep apnea with MAD or other dental appliance therapy may be mandated, either by the employer, a professional association, government body, or insurance provider. Although MAD devices are generally designed with consideration to patient comfort, there is a period where the patient must adjust to the new device, during which therapy is often abandoned due to irritation and discomfort. Thus, mere possession of a treatment device (for example, MAD or other dental appliance) is not sufficient to verify the patient has submitted to treatment recommendations. A recent statement on MADs from the American Trucking Association stated that there is evidence that MADs may help in reducing OSA in individuals with mild to moderate OSA there is no method of measuring compliance. Accurate confirmation of compliance may soon become a requirement for maintaining or renewing qualifications and licenses for some professions, and/or for obtaining reimbursement from a health insurance provider. Thus, there is a need to accurately know when a dental appliance such as a mandibular advancement device is being worn by a patient.

Devices disclosed in DuHamel et al US2010/0152599, Rahman et al US2006/0166157, Longley US2007/0283973, and Ivanov et al. U.S. Pat. No. 5,774,425 typically measure ambient temperature. Discussion of measuring other parameters such as oxygen saturation, light, pressure, movement, etc. are disclosed but methods of how to use these signals to increase accuracy of the oral compliance device are not disclosed.

Typical devices currently available for estimating compliance with MAD therapy and orthodontic treatments are battery-operated electronic devices that record only ambient temperature and are embedded within the oral appliance. These devices typically comprise a thermal sensor, a memory storage device, a battery power supply, a clock and an electronic processor. Such devices must, obviously, be of sufficiently small size to allow for embedding into the oral appliance, and preferably minimally increasing its size, so they do not add to patient discomfort or inhibit the effectiveness of the MAD in treating OSA. This limits the type of signals that may practically be recorded to those that can be measured with sensors having small size and low power consumption.

The simplest such systems record intra-oral temperatures using a suitable sensor (typically a thermistor) to determine whether they are within a range that is consistent with placement in the mouth of a patient.

One article titled "Applicative Characteristics of New Microelectronic sensors Smart Retainer and TheraMon for Measuring Wear Time" that appeared in Journal of Orofacial Orthopedics (Timm Cornelius Schott, Gernot Göz, J Orofac Otrhop (German Orthodontic Society) 2010; 71:339-47) compared the Smart sensor to the TheraMon sensor. This article explained how they tested the devices using a readily obtainable thermostatic water bath, a Buchi B-490 Heating Bath. By programming the water bath to heat the water to a temperature of 35° C. for a specified length of time and then allowing the temperature to fall to room temperature the authors were able to trick both sensors into reporting wear time during the time the water was heated to 35° C. This testing teaches the reader how to fool both the Smart and TheraMon sensors into thinking that they were in the mouth of a patient.

Both the Smart and TheraMon sensors sample a temperature signal once every 15 minutes. The Smart chip has a sensitivity of 0.3° C. and the TheraMon had a 0.1° C. In the article, the authours discuss that the TheraMon chip was more accurate because of the lower sensitivity.

Rules are expected to come down from several different sources, such as transportation authorities, health insurance companies and employers that require some form of accurate indication of when a MAD device is being worn. Current devices that use temperature only can be easily fooled. Similarly devices that rely on temperature only will have issues in functioning properly in warm environments. A compliance monitoring system that checks only whether the intra-oral temperature is within an acceptable range is easily deceived by creative individuals, for example, by placing it in a warm water bath, kept at a constant temperature with a heating device and thermostat during sleeping hours.

For example, Rahman et al. (US2006/0166157 A1) teaches a device that may use a combination of temperature, moisture, pH, light, and pressure measurements to make it more difficult to deceive the system. DuHamel et al. (US2010/0152599) teach an oral appliance that uses measurement of blood-oxygen saturation levels in the oral tissues to more accurately verify compliance. Abolfathi (U.S. Pat. No. 7,553,157 B2) teaches the use of a colorant indicator that reacts to temperature, moisture, and/or one or more intra-oral chemical or biological species. However, these additional measurements not only consume additional power, but in many cases, also involve different mechanical requirements, such as small openings to allow direct contact with the oral cavity and/or tissues, as is the case with pH, moisture, and species measurements. These openings are at risk of bacterial contamination which may then infect the patient.

Longley (US2007/0283973) teaches an oral appliance that responds to commands received via a transceiver to record measurements such as temperature, hydrogen ion concentration, pH, moisture, absolute humidity, or movement of oral appliance at periodic intervals. The recorded measurements are analyzed to determine if the measurements are consistent with the conditions expected in the oral cavity. Additionally, the recorded measurements are used to determine usage patterns as well as to determine if the user's use of the oral appliance has been in accordance with a patient's prescribed therapy schedule.

However, the above-described methods are susceptible to deception by users placing the dental appliance in artificial environments that mimic conditions in the oral cavity. The method of the present invention is devised to be difficult to deceive without requiring significant additional power and increasing the size of the device.

SUMMARY

The present disclosure allows for verification of compliance with dental appliance therapy with improved accuracy and/or reduced power consumption (i.e. longer product life) compared to existing devices.

In an aspect, the present disclosure provides a method for verifying compliance with a dental appliance therapy for a human patient comprising periodically measuring at least one parameter of a dental appliance worn by the human patient to obtain a time-domain series of measurements of the at least one parameter. At least a portion of the time-domain series of measurements is transformed to a frequency-domain series of measurements. Compliance with the dental appliance therapy is determined by determining that components of the frequency-domain series of measurements are within pre-selected tolerances to indicate compliance.

In an aspect, the present disclosure provides a dental appliance therapy compliance monitoring apparatus for use with a compliance verification processor. The apparatus comprises a battery to power the apparatus; a temperature sensor to measure an ambient temperature of the apparatus; a spatial orientation sensor to measure a spatial orientation of the apparatus; a processor configured to control the temperature sensor and the spatial orientation sensor to periodically measure the ambient temperature and the spatial orientation to obtain a time-domain series of ambient temperature measurements and a time-domain series of spatial orientation measurements, respectively; a memory operatively coupled to the processor to record the time-domain series of ambient temperature measurements and the time-domain series of spatial orientation measurements; and a communication module operatively coupled to the processor to communicate the recorded time-domain series of ambient temperature measurements and the recorded time-domain series of spatial orientation measurements to the compliance verification processor for determining compliance with the dental appliance therapy.

In an aspect, the present disclosure provides a compliance verification processor for use with a dental appliance therapy compliance monitoring apparatus as described herein. The compliance verification processor is configured to: transform at least a portion of the time-domain series of ambient temperature measurements to a frequency-domain series of ambient temperature measurements; and, determine compliance with the dental appliance therapy by determining that components of the frequency-domain series of ambient temperature measurements are within pre-selected tolerances to indicate compliance.

In another aspect, the compliance verification processor is configured to: transform at least a portion of the time-domain series of spatial orientation measurements to a frequency-domain series of spatial orientation measurements; and, determine compliance with the dental appliance therapy by determining that components of the frequency-domain series of the spatial orientation measurements are within pre-selected tolerances to indicate compliance.

In an aspect, the present disclosure provides a dental appliance therapy compliance verification system. The system comprises a dental appliance therapy compliance monitoring apparatus and a compliance verification processor. The dental appliance therapy compliance monitoring apparatus includes: a battery to power the apparatus; a temperature sensor to measure an ambient temperature of the apparatus; a spatial orientation sensor to measure a spatial orientation of the apparatus; a processor configured to control the temperature sensor and the spatial orientation sensor to periodically measure the ambient temperature and the spatial orientation to obtain a time-domain series of ambient temperature measurements and a time-domain series of spatial orientation measurements, respectively; a memory operatively coupled to the processor to record the ambient temperature measurements and the spatial orientation measurements; and a communication module operatively coupled to the processor. The compliance verification processor is configured to communicate with the communication module of the apparatus to communicate the recorded time-domain series of ambient temperature measurements and the time-domain series of spatial orientation measurements and to determine compliance with the dental appliance therapy.

In an aspect, the present disclosure provides a tangible computer-readable medium having recorded thereon non-transitory instructions, which when executed by a processor causes a computer to perform a method for verifying compliance with a dental appliance therapy for a human patient as described herein.

BRIEF DESCRIPTION OF THE DRAWINGS

Embodiments of the present disclosure will now be described, by way of example only, with reference to the attached Figures.

DETAILED DESCRIPTION

Figure 1:
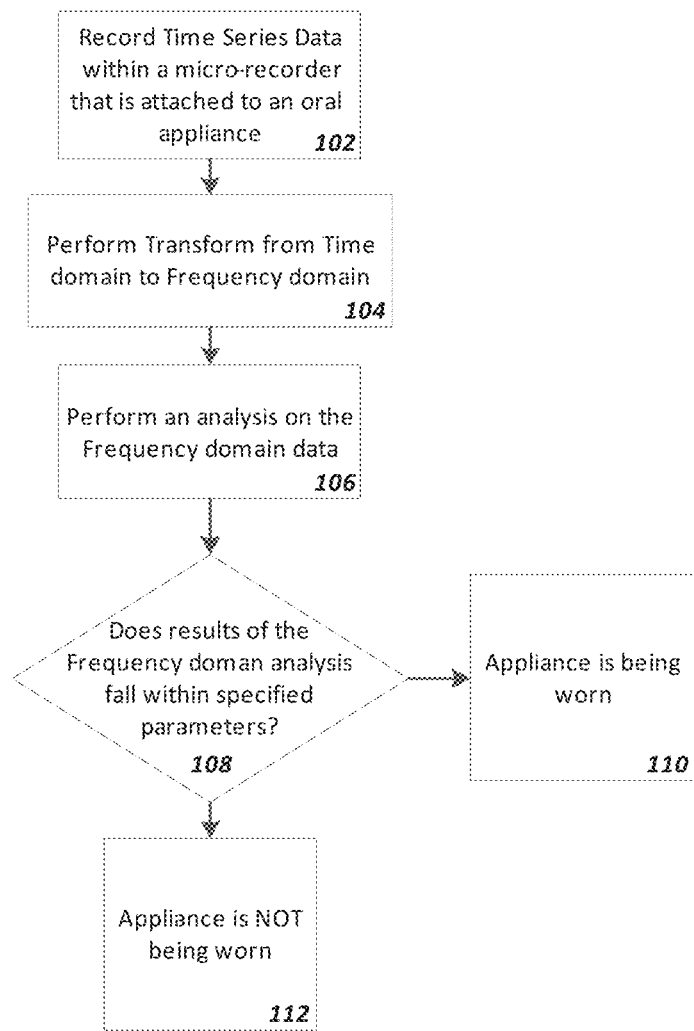
FIG. 1 is a flow diagram of a method for verifying compliance with a dental appliance therapy for a human patient in accordance to an aspect of the present disclosure.

Generally, the present disclosure provides a method and an apparatus for verifying compliance with a dental appliance therapy for a human patient by periodically measuring a parameter of a dental appliance worn by the human patient and determining compliance with the dental appliance therapy by performing a spectral analysis of the measured parameter.

For illustrative purposes, example embodiments of the present disclosure are described using temperature and/or spatial orientation of the dental appliance as the measured parameters. However, other parameters such as, humidity, pH, or other suitable intra-oral physiological parameters may also be used for determining compliance with the dental appliance therapy in accordance with the present disclosure.

In humans, the temperature inside the mouth closely approximates body core temperature the vast majority of time, and the typical range of intra-oral temperature is approximately 34-39 degrees Celsius. Thus, as a first indicator of compliance, the temperature value is checked to see if it is within this range. If the temperature recorded consistently lies outside this range, it is likely that the device is not being worn.

Instances when intra-oral temperature does not closely approximate body temperature include when hot or cold foods or beverages are being consumed, and during smoking. These activities, however, cannot be performed while asleep, and are therefore not relevant to the present disclosure. Additionally, the above temperature range does not account for instances of significant fever or hypothermia. However, such occurrences are rare, and are not deemed significant for the present purposes. One notable exception however is during oral breathing, when the intra-oral temperature only closely approximates body core temperature during exhalation. During oral inhalation, intra-oral temperature often is significantly lower than body core temperature. This may be circumvented by of consecutive measurements lie within the range 34-39 degrees Celsius.

However, as described earlier, methods of verifying compliance based on intra-oral temperature measurement or other parameters alone to determine if the measurements are consistent with the conditions expected in the oral cavity can be easily defeated using commonly available items.

In order to improve the accuracy of compliance verification, the present disclosure utilizes the differences in the spectral properties to verify compliance with the dental appliance therapy. The spectral properties of physiological parameters such as temperature have a different spectral signature than in an artificial mechanical environment such as a water bath that may be used to deceive compliance with the dental appliance therapy.

Accordingly, the present disclosure allows for verification of compliance with dental appliance therapy with improved accuracy and/or reduced power consumption (i.e. longer product life) compared to existing devices using spectral analysis of the measured parameters.

For example, FIG. 1 shows a flow diagram of a method for verifying compliance with a dental appliance therapy for a human patient in accordance to an aspect of the present disclosure. At least one parameter of a dental appliance worn by the human patient is periodically measured to obtain a time-domain series of measurements or data of the at least one parameter at 102. At least a portion of the time-domain series of measurements is transformed to a frequency-domain series of measurements or data at 104. The time domain data may be transformed into frequency domain data by suitable spectral transformation such as Fast Fourier Transformation (FFT), Discrete Fourier Transformation (DFT) or the like.

Components of the frequency-domain data, for example, amplitude, phase, power, etc., are analyzed at 106 to determine that whether the results of the frequency domain analysis fall within pre-selected tolerances or specified parameters at 108. If yes, it is determined at 110 that the dental appliance is worn by the human patient. Otherwise, it is determined at 112 that the appliance is not being worn by the human patient, indicating a potential lack of compliance with the dental appliance therapy.

Figure 2:
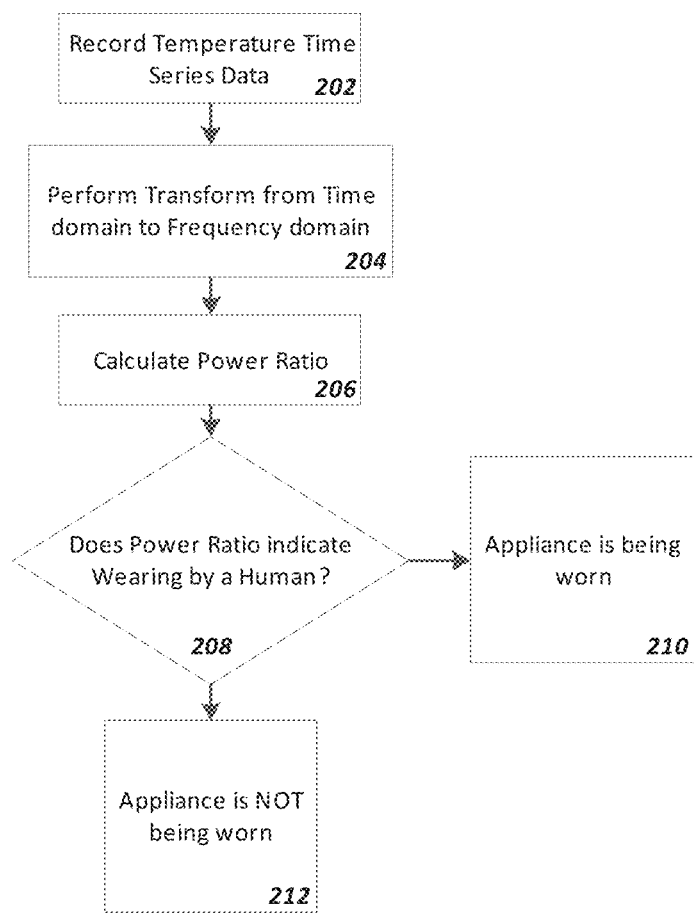
FIG. 2 is a flow diagram of a method for verifying compliance with a dental appliance therapy for a human patient using temperature by comparing the ratio of the power in two frequency bands to determine compliance in accordance with an example embodiment of the present disclosure.

In an example embodiment, the measured parameter may be intra-oral/ambient temperature. Time-domain temperature measurements can be transformed into frequency-domain data as described above. Compliance with the dental appliance therapy may be determined by comparing the ratio of the power in two frequency bands in the frequency-domain temperature measurements as shown in FIG. 2.

Temperature of the dental appliance worn by the human patient is periodically measured to obtain a time-domain series of temperature measurements at 202. At least a portion of the time-domain series of temperature measurements is transformed to a frequency-domain series of measurements at 204. A ratio of the total power in two frequency bands is calculated. Physiological temperature varies at a slower frequency than the temperature in an artificial mechanical environment such as a water bath that may be used to deceive compliance with the dental appliance therapy. Hence, frequency bands indicative of physiological frequency and mechanical frequency are selected for comparison.

A determination is made as to whether the ratio of the total power in the two frequency bands is within pre-selected tolerances at 208. If the ratio of total power is above a threshold value, it is determined at 210 that the dental appliance is worn by the human patient. Otherwise, it is determined at 212 that the appliance is not being worn by the human patient, indicating a potential lack of compliance with the dental appliance therapy.

Figure 3:
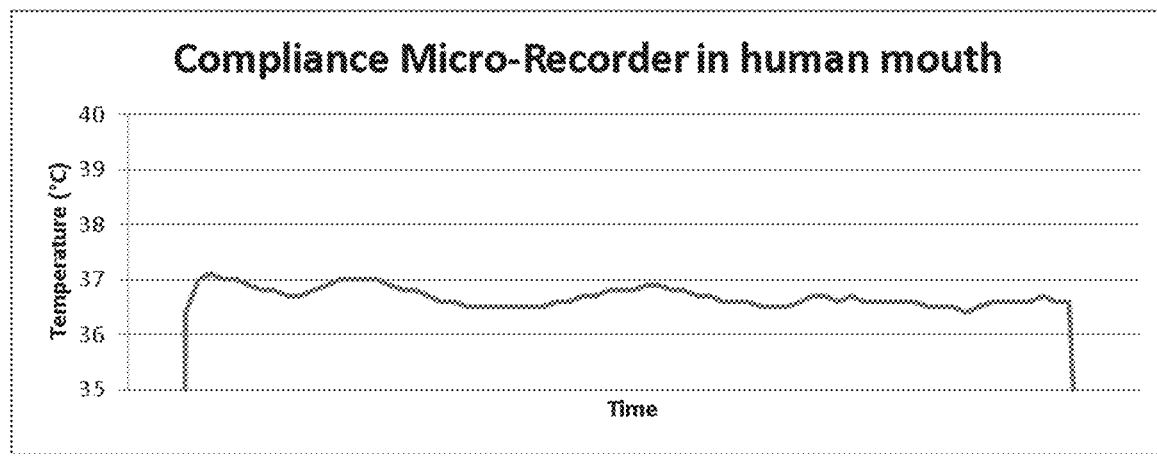
FIG. 3 is a time domain graph of temperature measurements recorded in a human mouth by a dental appliance therapy compliance monitoring apparatus in accordance with an example embodiment of the present disclosure.

FIG. 3 shows a time domain graph of temperature measurements recorded in a human mouth by a dental appliance therapy compliance monitoring apparatus, or a compliance micro-recorder, in accordance with an example embodiment of the present disclosure. The duration of the temperature measurements illustrated is about 6.5 hours.

Figure 4:
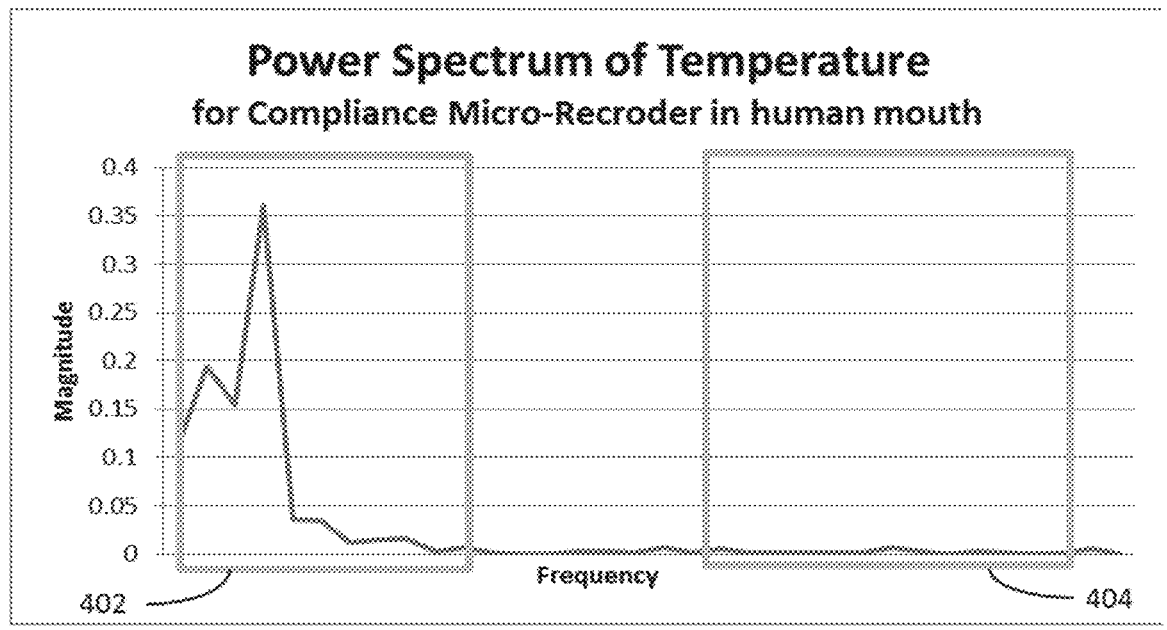
FIG. 4 is a frequency domain graph (Power Spectrum) of the transformed time domain series of temperature measurements in FIG. 3. Examples of two frequency bands used to calculate the power ratio for compliance determination in accordance with an example embodiment of the present disclosure are also shown in FIG. 4.

FIG. 4 shows a frequency domain graph (Power Spectrum) of the transformed time domain series of temperature measurements in FIG. 3. Examples of two frequency bands used to calculate the power ratio for compliance determination in accordance with an example embodiment of the present disclosure are also shown in FIG. 4.

The total power is calculated for all frequencies in the physiological frequency band 402 and the mechanical frequency band 404. If the ratio of total power is below a threshold value, it is determined that the dental appliance is worn by the human patient.

Figure 5:
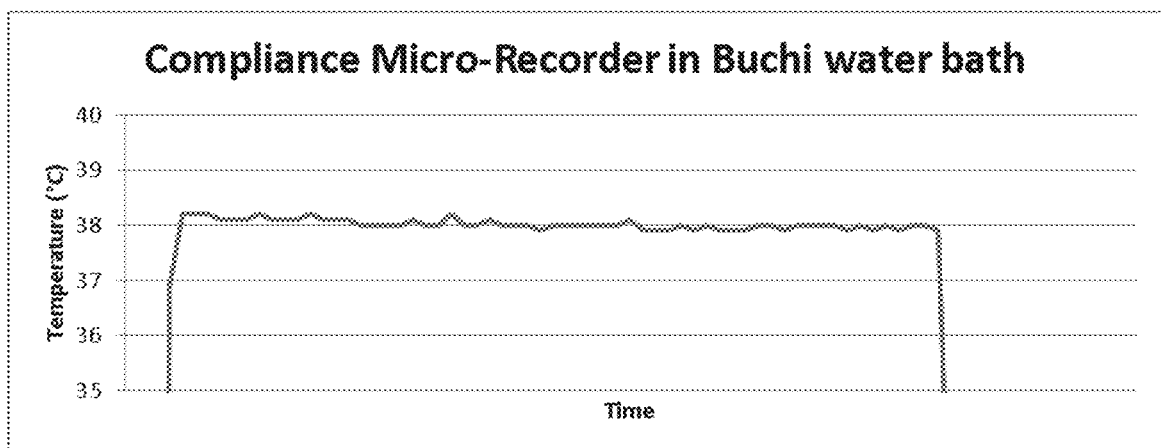
FIG. 5 is a time domain graph of temperature measurements recorded in an artificial environment (Buchi water bath) by a dental appliance therapy compliance monitoring apparatus in accordance with an example embodiment of the present disclosure.

FIG. 5 is a time domain graph of temperature measurements recorded in an artificial environment (Buchi water bath) by the dental appliance therapy compliance monitoring apparatus in accordance with an example embodiment of the present disclosure. The duration of the temperature measurements illustrated is about 6.5 hours, similar to the data shown in FIG. 3.

Figure 6:
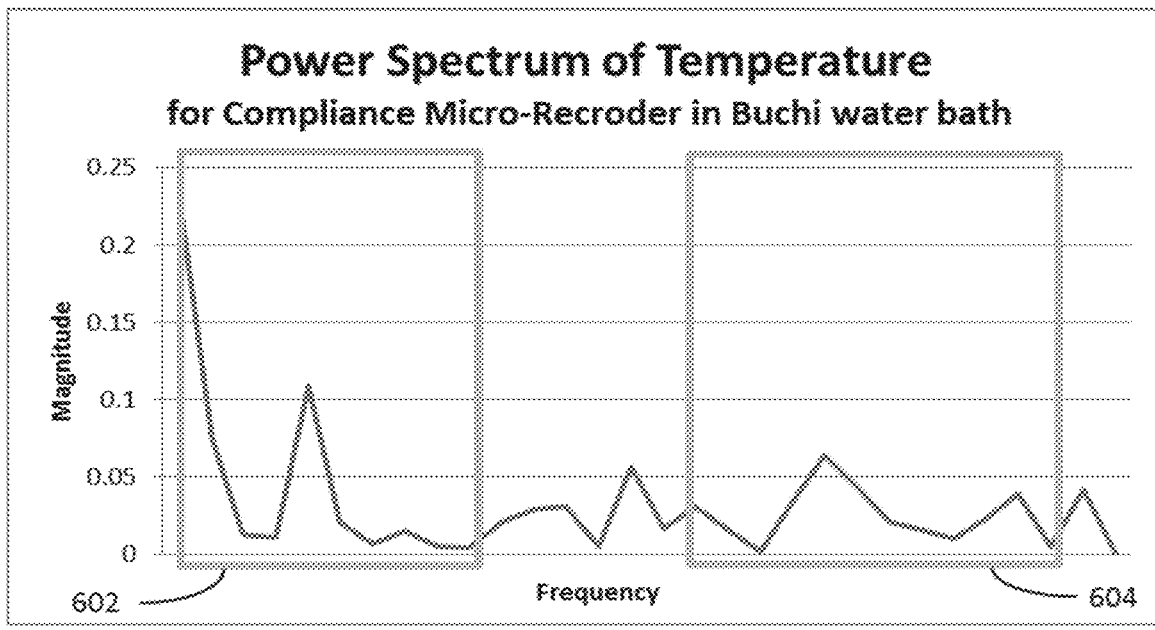
FIG. 6 is a frequency domain graph (Power Spectrum) of the transformed time domain series of temperature measurements in FIG. 5. Examples of two frequency bands used to calculate the power ratio for compliance determination in accordance with an example embodiment of the present disclosure are also shown in FIG. 6.

The time domain temperature data is transformed into frequency domain by suitable spectral transformation and is illustrated in FIG. 6. The total power is calculated for all frequencies in the physiological frequency band 602 and the mechanical frequency band 604. It can be seen that the spectral signature of the temperate measurements in the artificial environment (FIG. 6) is significantly different than spectral signature of the temperature measurements in the oral cavity of a human patient (FIG. 4). The difference is exemplified in the in the total power in the mechanical frequency band 604. Thus, a ratio of the total power in the two frequency bands in the example of FIG. 6 would be greater than that obtained in the example of FIG. 4, indicating non-compliance with the dental appliance therapy.

In another example embodiment, the measured parameter may be the spatial orientation of the dental appliance. Time-domain spatial orientation measurements can be transformed into frequency-domain data as described above. Compliance with the dental appliance therapy may be determined by calculating the mean or average power of the power spectrum of the spatial orientation measurements.

Figure 7:
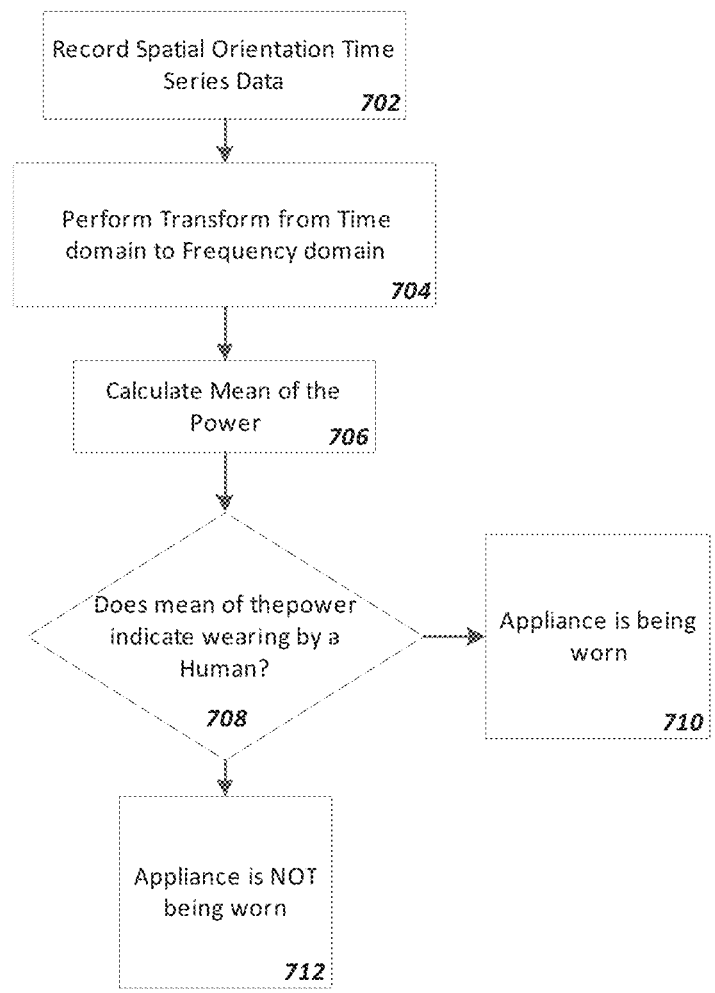
FIG. 7 is a flow diagram of a method for verifying compliance with a dental appliance therapy for a human patient using spatial orientation by comparing the mean of the total power to a threshold level to determine compliance in accordance with an example embodiment of the present disclosure.

As shown in FIG. 7, the spatial orientation of the dental appliance worn by the human patient is periodically measured to obtain a time-domain series of spatial orientation measurements at 702. At least a portion of the time-domain series of spatial orientation measurements is transformed to a frequency-domain series of measurements at 704. The mean or average power of the power spectrum of the spatial orientation measurements is calculated at 706. A determination is made as to whether the average power is above a threshold value at 708. If the average power is above the threshold value, it is determined at 710 that the dental appliance is worn by the human patient. Otherwise, it is determined at 712 that the appliance is not being worn by the human patient, indicating a potential lack of compliance with the dental appliance therapy.

Figure 8:
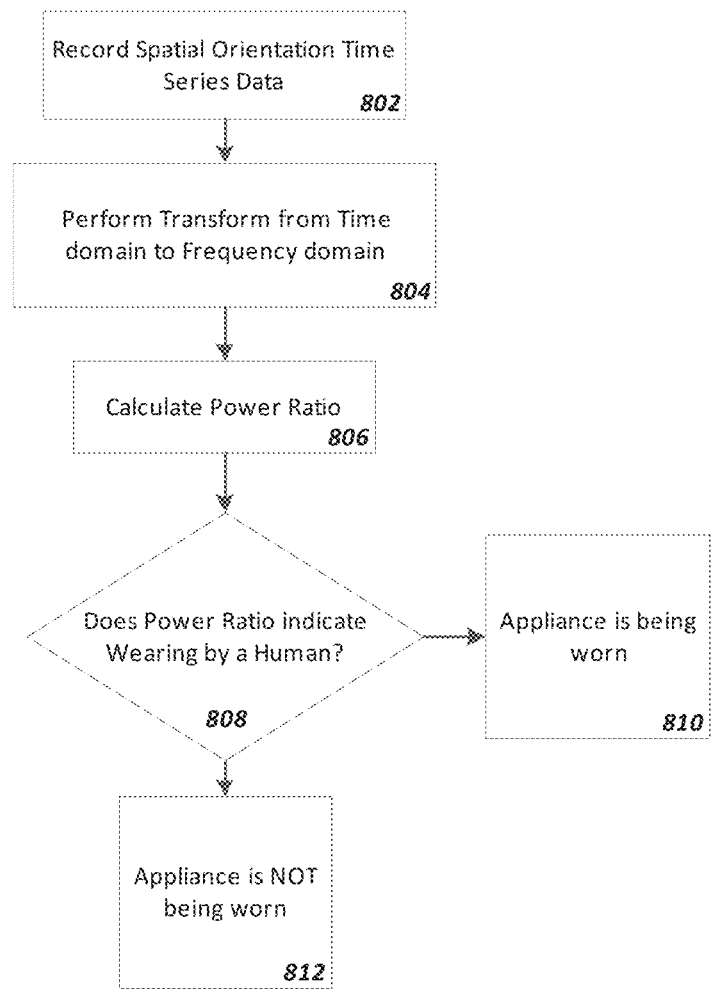
FIG. 8 is a flow diagram of a method for verifying compliance with a dental appliance therapy for a human patient using spatial orientation by comparing the ratio of the power in two frequency bands to determine compliance in accordance with an example embodiment of the present disclosure.

In another example embodiment, compliance with the dental appliance therapy may be determined by comparing the ratio of the power in two frequency bands of the frequency-domain series of measurements of spatial orientation to determine compliance as shown in FIG. 8.

The spatial orientation of the dental appliance worn by the human patient is periodically measured to obtain a time-domain series of spatial orientation measurements at 802. At least a portion of the time-domain series of spatial orientation measurements is transformed to a frequency-domain series of measurements at 804. A ratio of the total power in two frequency bands is calculated at 806. Physiological spatial orientation varies differently than the spatial orientation in an artificial mechanical environment that may be used to deceive compliance with the dental appliance therapy. Hence, frequency bands indicative of physiological frequency and mechanical frequency are selected for comparison.

A determination is made as to whether the ratio of the total power in the two frequency bands is within pre-selected tolerances at 808. If the ratio of total power is within pre-selected tolerances, it is determined at 810 that the dental appliance is worn by the human patient. Otherwise, it is determined at 812 that the appliance is not being worn by the human patient, indicating a potential lack of compliance with the dental appliance therapy.

Figure 9:
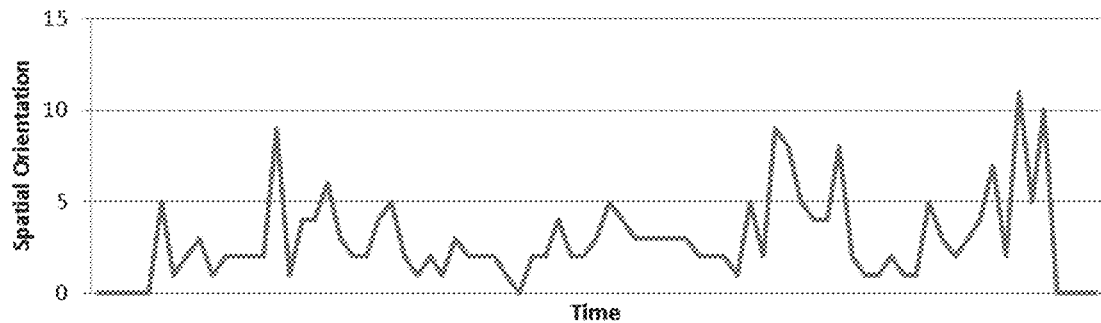
FIG. 9 is a time domain graph of the spatial orientation measurements recorded in a human mouth by a dental appliance therapy compliance monitoring apparatus in accordance with an example embodiment of the present disclosure.
Figure 10:
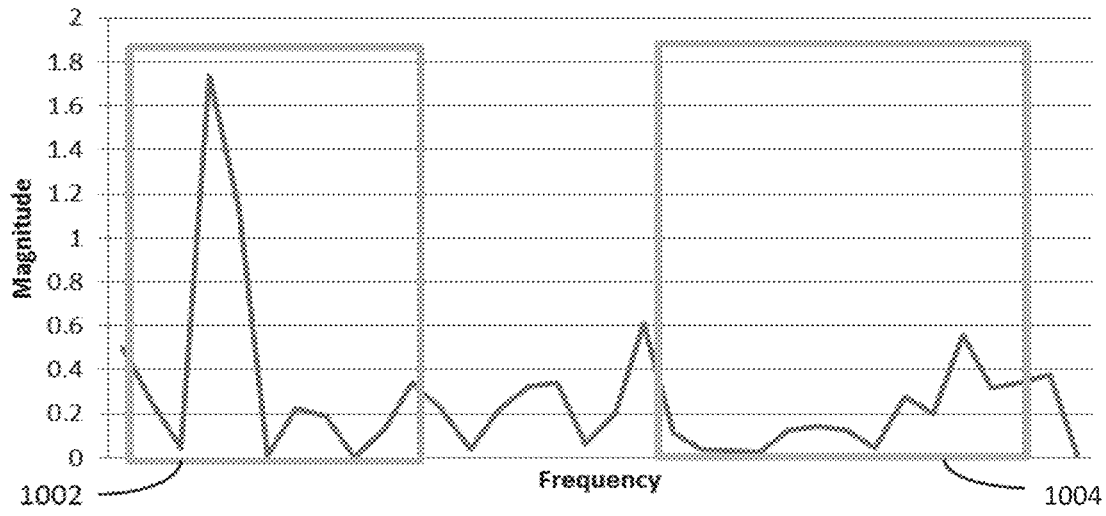
FIG. 10 is a frequency domain graph (Power Spectrum) of the transformed time domain series spatial orientation measurements in FIG. 9.

FIG. 9 shows a time domain graph of spatial orientation measurements recorded in a human mouth by a dental appliance therapy compliance monitoring apparatus, or a compliance micro-recorder, in accordance with an example embodiment of the present disclosure. The time domain spatial orientation data is transformed into frequency domain by suitable spectral transformation. FIG. 10 shows a frequency domain graph (Power Spectrum) of the transformed time domain series of spatial orientation measurements in FIG. 9. Examples of two frequency bands used to calculate the power ratio for compliance determination in accordance with an example embodiment of the present disclosure are also shown in FIG. 9.

The total power is calculated for all frequencies in the physiological frequency band 1002 and the mechanical frequency band 1004. If the ratio of total power is below a threshold value, it is determined that the dental appliance is worn by the human patient.

Figure 11:
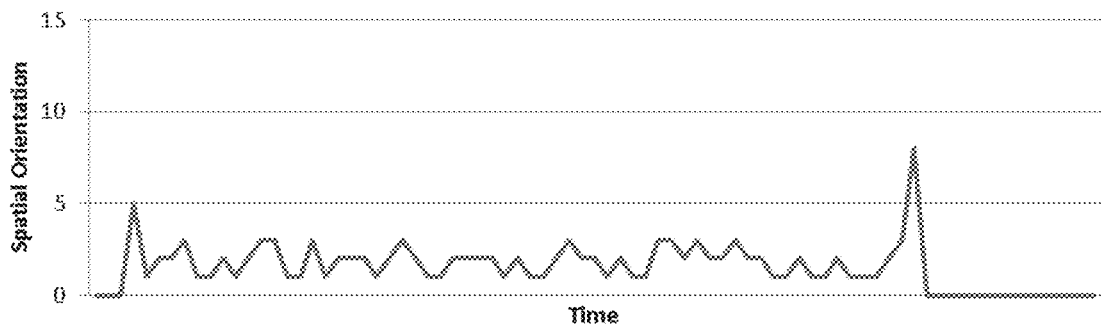
FIG. 11 is a time domain graph of the spatial orientation measurements recorded in an artificial environment (Buchi water bath) by a dental appliance therapy compliance monitoring apparatus in accordance with an example embodiment of the present disclosure.

FIG. 11 is a time domain graph of spatial orientation measurements recorded in an artificial environment (Buchi water bath) by the dental appliance therapy compliance monitoring apparatus in accordance with an example embodiment of the present disclosure.

Figure 12:
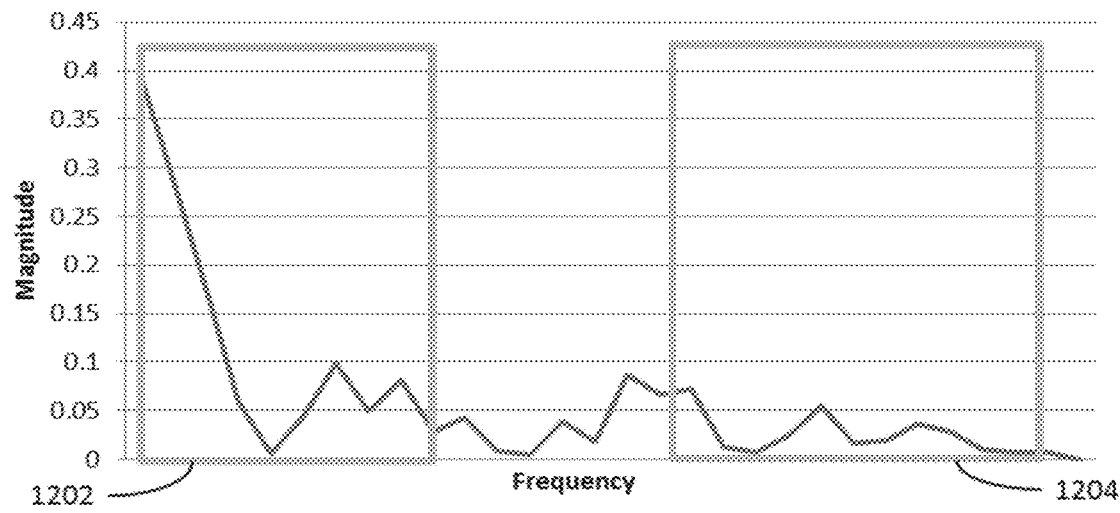
FIG. 12 is a frequency domain graph (Power Spectrum) of the transformed time domain series of spatial orientation measurements in FIG. 11. Examples of two frequency bands used to calculate the power ratio for compliance determination in accordance with an example embodiment of the present disclosure are also shown in FIG. 12.

The time domain spatial orientation data is transformed into frequency domain by suitable spectral transformation and is illustrated in FIG. 12. The total power is calculated for all frequencies in the physiological frequency band 1202 and the mechanical frequency band 1204. It can be seen that the spectral signature of the spatial orientation measurements in the artificial environment (FIG. 12) is significantly different than spectral signature of the spatial orientation measurements in the oral cavity of a human patient (FIG. 10). The difference is exemplified in the in the total power in the mechanical frequency band 1204. Thus, a ratio of the total power in the two frequency bands in the example of FIG. 12 would be different than that obtained in the example of FIG. 10, indicating non-compliance with the dental appliance therapy.

In an example embodiment, compliance with the dental appliance therapy may be verified by analyzing the power spectrum of the frequency-domain spatial orientation measurements and determining that it is random. Additionally, compliance may be verified by determining that the power spectrum lacks any significant frequency or frequencies indicative of a change in spatial orientation due to an artificial means.

In an example embodiment, the present disclosure uses two measurements, for example, intra-oral/ambient temperature and the spatial orientation measurements. The spatial orientation measurements may be, for example, the x, y, z coordinates of the direction of gravity (gravity vector) as measured by an accelerometer.

Figure 13:
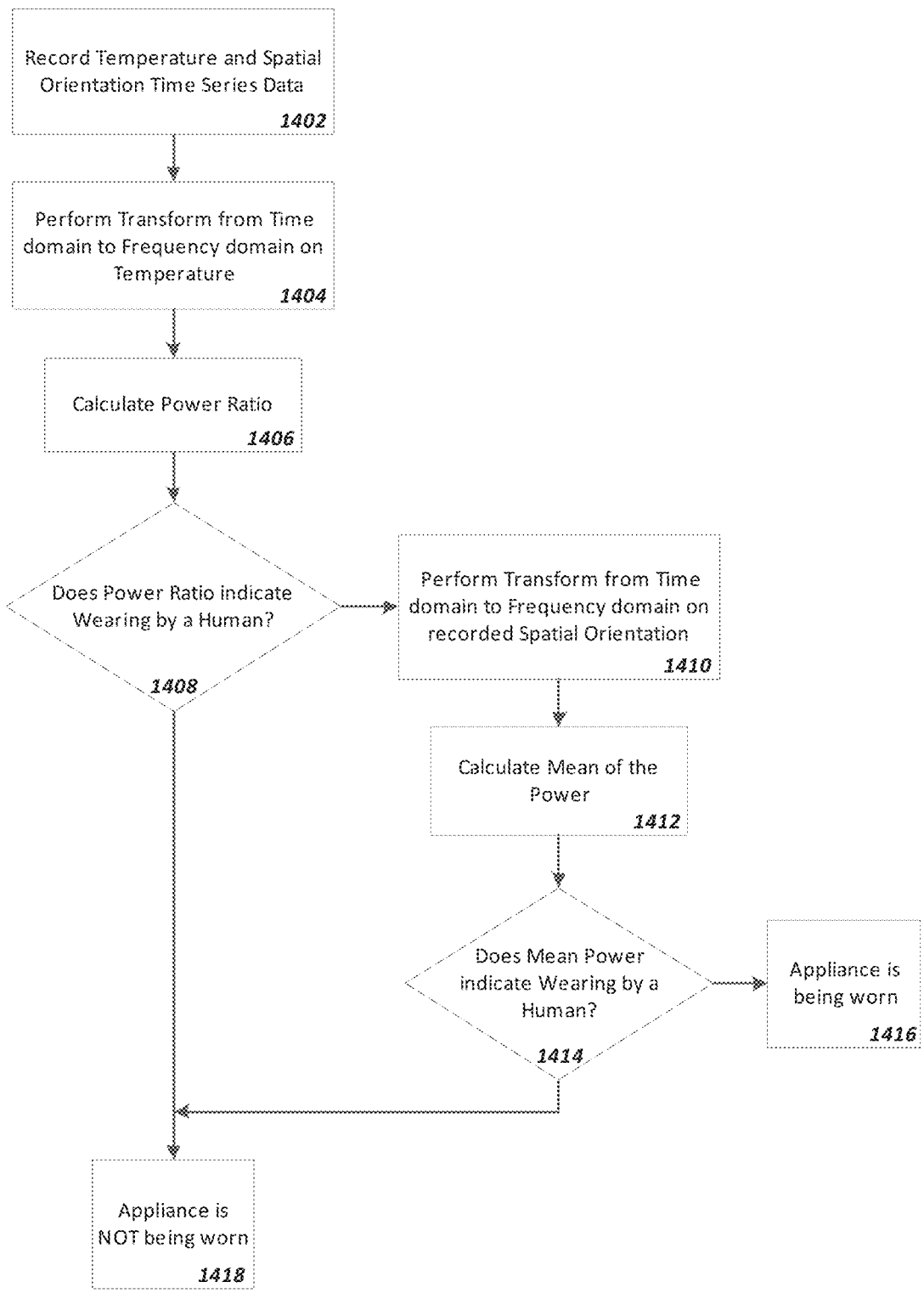
FIG. 13 is a flow diagram combining the method in FIG. 2 with the method in FIG. 7.

FIG. 13 is a flow diagram combining the method in FIG. 2 with the method in FIG. 7. Temperature and spatial orientation of the dental appliance worn by the human patient is periodically measured to obtain a time-domain series of temperature and spatial orientation measurements at 1402. At least a portion of the time-domain series of temperature measurements is transformed to a frequency-domain series of temperature measurements at 1404. A ratio of the total power in two frequency bands is calculated at 1406. A determination is made as to whether the ratio of the total power in the two frequency bands is within pre-selected tolerances at 1408. If the ratio of total power is above a threshold value, at least a portion of the time-domain series of spatial orientation measurements is transformed to a frequency-domain series of spatial orientation measurements at 1410. The mean or average power of the power spectrum of the spatial orientation measurements is calculated at 1412. A determination is made as to whether the average power is above a threshold value at 1414. If the average power is above the threshold value, it is determined at 1416 that the dental appliance is worn by the human patient. Otherwise, it is determined at 1418 that the appliance is not being worn by the human patient, indicating a potential lack of compliance with the dental appliance therapy.

It is noted that other example embodiments may combine the method of FIG. 2 with the method of FIG. 8. All three methods may also be combined to determine compliance with the dental appliance therapy.

The combination of intra-oral temperature measurements with a secondary signal such as spatial orientation as a co-indicator of compliance may further improve the accuracy of the compliance verification method and apparatus of the present disclosure. For example, the orientation of the patient relative to the local gravity vector may be used as a parameter for compliance verification alone (as described earlier with reference to spatial orientation) or in combination with temperature measurements. If the device orientation indicates consistency with a substantially upright or upside-down patient, it is very likely that (i) the device is not being worn, or (ii) the patient is not asleep.

Additional co-indicators are optionally derived from the intra-oral temperature measurements, and the device orientation measurements. In an example embodiment, the variation of temperature over time and the change of the orientation of the gravity vector is computed. The four derived signals from the measurement of two physiological phenomena consist of current ambient temperature, a delta temperature that shows the largest magnitude in temperature change from the last reading, head position (standing, prone, supine, left or right) and head movement which may be derived, for example, from the largest change in 2 dimensions of the gravity vector from the last recorded sample.

In another example embodiment, an autocorrelation of the recorded temperature is performed for the period(s) during which the temperature is consistent with intra-oral placement. The result of the autocorrelation is compared to acceptable values for biological signals. This differentiates quasi-random metabolic temperature variations from the regular temperature variations typical of thermostatically-controlled heating devices commonly used to deceive compliance monitors.

An autocorrelation of the recorded orientation signal is also performed in another example embodiment, for the period(s) during which at least one other signal or indicator is consistent with intra-oral placement and a sleeping patient. The autocorrelation differentiates quasi-random movements of a human patient during sleep from programmed and/or motorized artificial movements which may be used to deceive the compliance monitor.

A standard statistical measure of deviation of the recorded orientation signal is also preferably performed for the period(s) during which at least one other signal or indicator is consistent with intra-oral placement and a sleeping patient. The variation of the orientation signal, when the device is worn, indicates the extent of head movement of the patient. During sleep, a certain minimum level of activity is expected. If the signal variation is below this minimum level, it is very likely that the device is not being worn. Conversely, a high level of activity is not sustainable during sleep. Thus, in an example embodiment, the level of activity within a range bounded by a minimum value and a maximum value indicates the patient to be in compliance with the dental appliance therapy.

To conserve power and memory, thus reducing the required physical size of the battery and memory storage device, the measured signals need not be sampled continuously. Instead, in an example embodiment, short measurement bursts are taken at intervals, and the device may be put into a dormant mode between bursts, with only the system clock active. Appropriate measurement intervals may be in the range of 30-300 seconds, with virtually no loss of significance of the results.

To further reduce the memory requirement, data may be stored to memory at pre-selected intervals of measurement bursts. Wth this method, a sequence of measurement bursts is stored in a temporary memory location. Once the pre-selected storage interval is reached, a mean value of the measurements is computed, and a statistical measure of the variance of the same values is computed. These data are then stored to memory in lieu of the individual measurements. In an example embodiment, data are stored every fifth measurement burst, reducing the memory requirement by 60%, but without substantial loss of significance.

As is the case with other devices, the primary indicator of compliance is intra-oral temperature. Intra-oral temperature is typically measured with a thermistor. These devices are relatively low in cost, widely available, and provide stable output over long periods of time. It is noted, however, that the various aspects of the present disclosure work equally well with temperature measured by any other means.

Thermistors typically consume power to produce an electrical output. To conserve battery power, the thermistor is only powered for a short time before, during, and after data acquisition. In an example embodiment, the thermistor is powered for less than one millisecond for each measurement burst, and measurement bursts are taken at intervals of one minute. Sampling at intervals instead of continuously also conserves device memory. As an additional means of conserving memory, in an example embodiment, data are stored at five-minute intervals. The data stored are the output at the first minute, and the absolute maximum of the difference between that measurement and the measurements at the second, third, fourth, and fifth minutes. Because two data are stored instead of five, this method of data storage reduces the required storage capacity by 60%, without significant loss of generality of the results.

As described earlier, methods of verifying compliance based on intra-oral temperature measurement or other parameters alone to determine if the measurements are consistent with the conditions expected in the oral cavity can be easily defeated using commonly available items.

The spectral analysis methods described herein improve the accuracy of compliance verification. In addition, the use of at least one appropriate secondary signal further improves the accuracy of compliance verification. The example embodiments of the present disclosure have been described using temperature and spatial orientation as two parameters used for compliance verification.

Spatial orientation may be provided by a suitable accelerometer. In an example embodiment, a three-axis capacitive accelerometer is used. If inertial effects are ignored or deemed insignificant, as is usually the case during sleep, the accelerometer signal indicates its orientation with respect to the direction of gravity. Additionally, the signal may be used to estimate the extent of its movement during a time interval, by taking the difference between consecutive measurements. Finally, capacitive accelerometers are widely available at relatively low cost, and require little power to operate. Thus, use of these instruments is consistent with the requirements of low power consumption, and acquisition of data from which device position and movement may be quantified.

Figure 14:
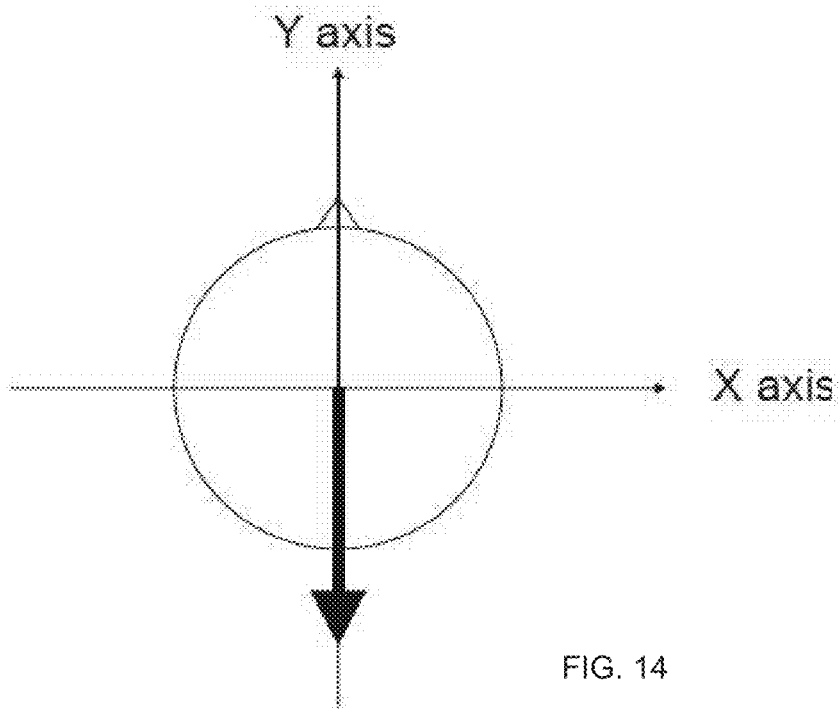
FIG. 14 shows a diagram of a patients head in the supine position with labeled X and Y axis and gravity vector.
Figure 15:
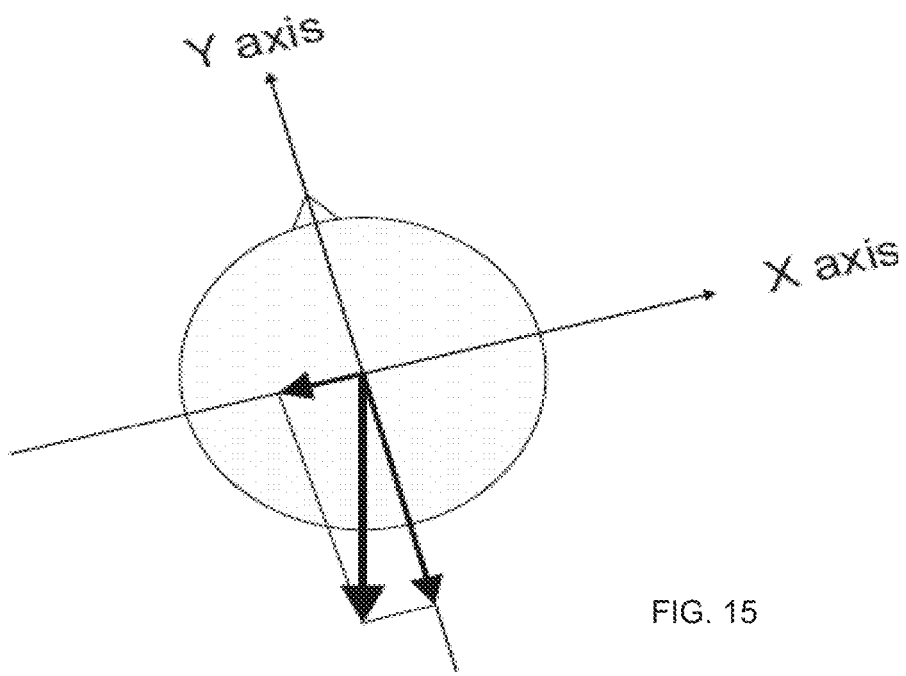
FIG. 15 shows a diagram of a patients head in the supine partial left position with labeled X and Y axis, gravity vector and the X and Y components of the gravity vector.
Figure 16:
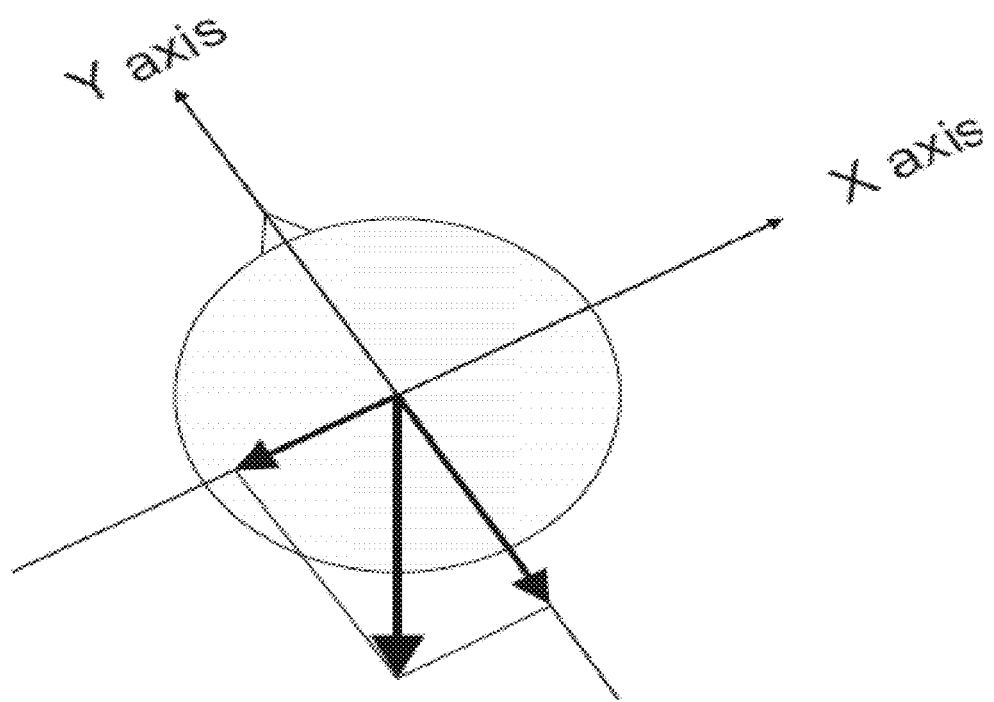
FIG. 16 shows a diagram of a patients head in the supine—left position with labeled X and Y axis, gravity vector and the X and Y components of the gravity vector.

Spatial orientation of the device is computed by resolving the outputs of the three perpendicular accelerometer axes into a vector, which represents the direction of gravitation, as shown in FIGS. 14-16. When a dental appliance equipped with a 3-axis accelerometer is being worn, with the accelerometer fixed relative to the head of the patient, the orientation and movement of the accelerometer is the same as the orientation and movement of the patient's head. A convenient method of fixing the accelerometer relative to the head of the patient is for it to be rigidly embedded into the mandibular advancement device with a known orientation. Because the appliance, when worn, is always in the same position relative to the patient's head, this method also provides a fixed frame of reference for calculating the orientation of the patient's head, and the orientation of the device has a one-to-one correspondence with the orientation of the patient when wearing the device.

The design of the overwhelming majority of mandibular advancement devices and orthodontic appliances is such that when they are not worn, and are at rest on a flat surface, the only stable positions correspond to orientations with respect to gravity that would indicate a vertical position of the patient's head (i.e. as though standing upright or upside-down), as shown in FIG. 14. Thus, the most common and logical orientation of the device when it is not being worn is the least common and least logical orientation of the device when it is being worn and the patient is asleep. Therefore, the orientation of the device provides an effective indication of whether the device is being worn during sleep i.e., supine, prone, left or right positions.

An additional indicator of compliance can be derived from the variation in the spatial orientation signal over time. The variation of the spatial orientation signal, when the device is worn, indicates the extent of head movement of the patient. As the patient changes position, the accelerometer will indicate the new position of the gravitational vector relative to the oral appliance. A non-zero difference between consecutive orientation measurements indicates movement of the device in the intervening period. The magnitude of the difference indicates the magnitude of the movement or change in position. A small difference may indicate a small shift of the head, or opening of the jaw, for example, while a large difference typically indicates rolling over, or other whole-body movements. Thus, it is not only the frequency, but the magnitude of change in the orientation that is of significance. A suitable quantity that increases both with the frequency and magnitude of orientation change is the root-mean-squared value or standard deviation of several consecutive measurements.

During sleep, a certain minimum level of activity is expected. If a suitable measure of signal variation indicates activity below this minimum level, it is very likely that the device is not being worn. Conversely, a high level of activity is not sustainable during sleep. Thus, in an example embodiment, the measure of signal variation indicating activity level must lie within a range bounded by a minimum value and a maximum value in order for the patient to be considered in compliance. Another indication that the oral appliance is not being worn would be any periodic movements that are repeated over a given time. This would indicate that the device is in some form of mechanical apparatus and is in fact being fooled into thinking that it is being worn.

The spatial orientation information may be used by the clinician to assist patients with positional sleep apnea. Positional sleep apnea is the prevalence of sleep apnea in a specific sleep position. Typically positional sleep apnea is denoted as the patient having abnormal breathing while they are in the supine position (lying on their backs). Recording the spatial orientation of the head is required in order to determine the amount of time the patient is in a certain position. This information can be used by the clinician who is treating positional sleep apnea to if the patient is following instructions to type to reduce their amount of time in a specific position.

The spatial orientation signal can also be used to eliminate those individuals who wear the device but are not in a position to allow them to go to sleep. This aids in reducing the chance of deceiving the dental appliance therapy.

In an example embodiment, temperature, temperature difference and head position measurements are made at periodic intervals, from which head movement over time, and temperature changes or variation (delta temperature) can be determined. Based on this data, certain indicators of compliance can be determined or analyzed. The indicators of compliance can include, for example, a temperature that is consistently within a range indicating that the device is the oral cavity, such as measured or average temperatures above 34 C; a head position that indicates the user is not standing (or not standing upside down); temperature variations that show no evidence of mechanical intervention, such as heating in a thermostatically controlled water bath; and, head movements that are not static, and do not indicate evidence of mechanical intervention. If any of the indicators are negative, the patient is likely not complying with the dental appliance therapy.

It is noted that between consecutive orientation measurements that are different, it is not possible to determine the extent of movement, or, equivalently, the number of position changes that have occurred. Thus, it is acknowledged that the variance in orientation is an indication only, and not a measure of all activity. However, the measurement of 1 minute intervals over a 5 minute period is appropriate for capturing most movements during sleep. Thus, non-continuous sampling is justified for the present purposes, provided that the above is understood. Other devices typically record on single 5 minute or longer sample period.

To further conserve power, a short measurement burst is taken at appropriate intervals, instead of continuously sampling the accelerometer output. In an example embodiment of the present invention, single measurements are taken at intervals of one minute, and each measurement requires the accelerometer to be powered for less than one millisecond. This method also conserves device memory. As an additional means of conserving memory, in an example embodiment, data are stored at five-minute intervals. The data stored are the output at the first minute, and the absolute maximum of the difference between that measurement and the measurements at the second, third, fourth, and fifth minutes. Because two data are stored instead of five, this method of data storage reduces the required storage capacity by 60%, without significant loss of generality of the results. Data storage for a measurement cycle can be reduced to 2 bytes.

An additional means of compliance verification can be derived from a measure of the variation of temperature over time. One easy and widely accessible means of maintaining a relatively constant temperature of the device is immersion in a thermal bath, or other thermostatically controlled device. However, in such instances, we expect to see periodic increases and decreases in temperature, as the heating element is switched on and off. When the ambient temperature is relatively constant, the switching on and off of the element will occur at regular intervals.

This type of variation can be recognized by computing the autocorrelation of the signal for various values of lag, and searching for the maximum. Autocorrelation provides an indication of the similarity of a signal with a time-shifted version of itself. If the time shift, or lag, is close to a frequency of significance in the signal, the autocorrelation will have a large value, and if the lag is not close to any frequencies present in the signal, the autocorrelation will have a small value. The value of lag for which the autocorrelation has the largest value indicates the dominant frequency in the signal. If this dominant frequency is small (close to the sampling frequency), it may indicate that the signal is uncorrelated (random) or weakly correlated.

Although regular body-temperature variations are expected (due, for example to the circadian rhythm), they are not expected to auto-correlate with the same lag or dominant frequency as the switching on and off of the heating element of a thermostatically controlled device. Thus, if a strong temperature signal auto-correlation exists in this range and/or a frequency analysis of the delta temperatures demonstrates a significant frequency in the power spectrum that it is very likely that the device resides in a thermostatically heated environment, and therefore is not being worn. Further, compliance may be determined based on temperature measurements that indicate an expected nocturnal/diurnal variation in body temperature, as measured intra-orally.

An additional means of compliance verification is obtained by computing the autocorrelation of the accelerometer signal for various values of lag, and searching for the lag which yields the maximum autocorrelation factor. Movement during sleep occurs at quasi-random intervals, which would appear uncorrelated, or weakly correlated, for all values of lag. However, a robotic or motorized mechanism to periodically change the position of the device outside the patient's mouth, unless very sophisticated, would repeat a pattern of motions, yielding a strong autocorrelation factor when the lag coincides with the period of repeated motion.

In an example embodiment, compliance with treatment is determined from up to four parameters, recorded at approximately five (5) one (1) minute intervals: (i) a base temperature representative of the interval; (ii) a base spatial orientation representative of the interval; (iii) a maximum temperature variation during the interval; and (iv) a maximum spatial orientation variation during the interval. Additionally, autocorrelation of the temperature and spatial orientation signals, and a statistical measure of variance of the spatial orientation signal are computed after the data are retrieved from the device. For the device to register compliance: i) the recorded temperature must be between a specified range i.e., 35 degrees Celsius and 40 degrees Celsius ii) the spatial orientation must indicate a position that is not substantially vertical; iii) the statistical variance of the spatial orientation must be greater than a minimum value and less than a maximum value; iv) a sequence of temperature measurements spanning a specified period must not be strongly auto-correlated with a minimum and a maximum period; and v) a sequence of spatial orientation measurements spanning an specified period must not be strongly auto-correlated with a minimum and a maximum period.

Figure 17:
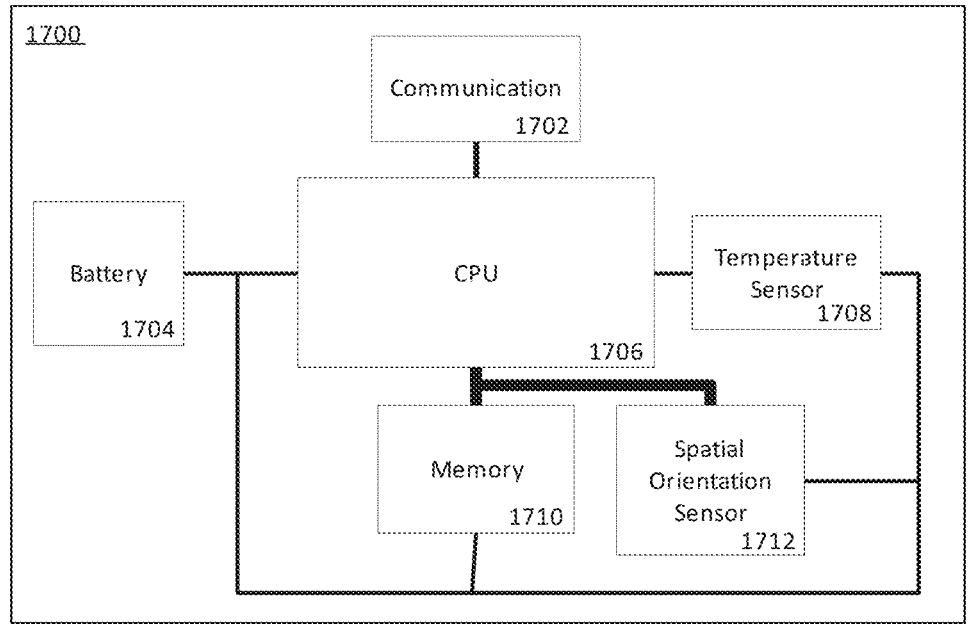
FIG. 17 is a block diagram of a dental appliance therapy compliance monitoring apparatus for a human patient in accordance with an aspect of the present disclosure.

FIG. 17 shows a block diagram of a dental appliance therapy compliance monitoring apparatus 1700 for a human patient according to an example embodiment. The apparatus 1700 consists of a battery 1704, CPU 1706, temperature sensor 1708, spatial orientation sensor 1712, a memory 1710 and a communications module 1702. The battery 1704 powers the apparatus 1700 and may be a disposable batter or a rechargeable battery. The temperature sensor 1708 measures an ambient temperature of the apparatus. The spatial orientation sensor 1712 measures a spatial orientation of the apparatus. The CPU 1706 is configured to control, among others, the temperature sensor 1708 and the spatial orientation sensor 1712 to periodically measure the ambient temperature and the spatial orientation to obtain a time-domain series of ambient temperature measurements and a time-domain series of spatial orientation measurements, respectively. The memory 1710 is operatively coupled to the processor 1706 to record the time-domain series of ambient temperature measurements and the time-domain series of spatial orientation measurements. The communication module 1702 is operatively coupled to the processor 1706 to communicate the recorded time-domain series of ambient temperature measurements and the time-domain series of spatial orientation measurements to an compliance verification processor (not shown) to determine compliance with the dental appliance therapy.

In an example embodiment, the compliance verification processor is configured to execute the methods as described herein.

Figure 18:
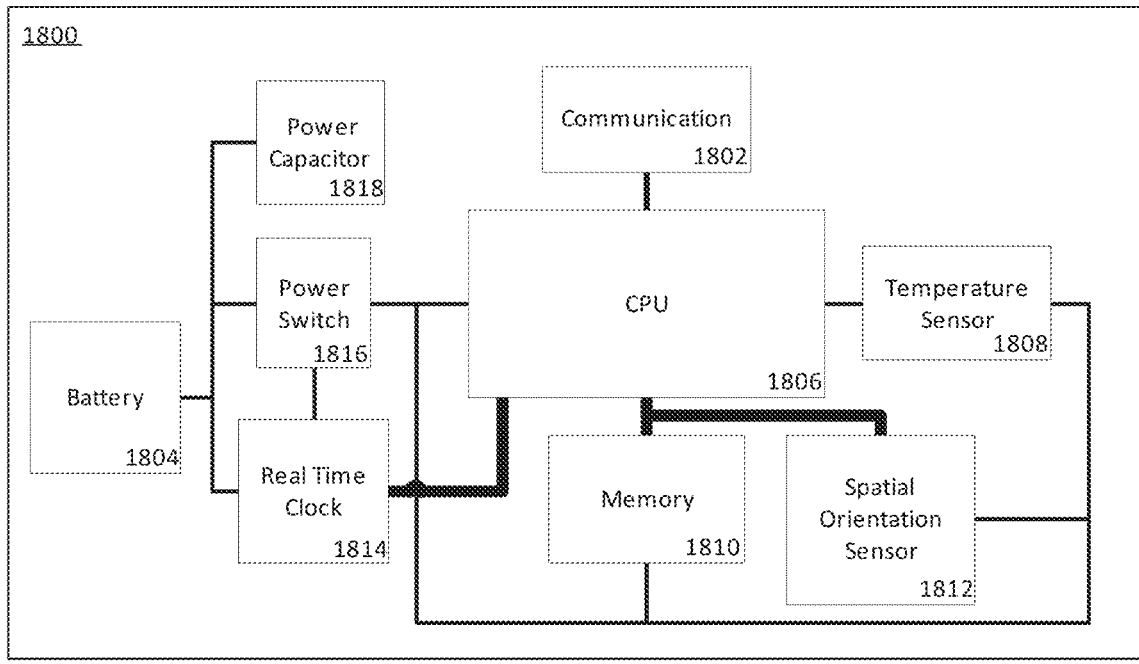
FIG. 18 is a block diagram of a dental appliance therapy compliance monitoring apparatus for a human patient having its power turned on and off by a real-time clock in accordance with an example embodiment of the present disclosure.

In an example embodiment, the apparatus may further include a real time clock; a power switch; and a power capacitor as shown in FIG. 18. As described earlier, the apparatus described herein have reduced power consumption. This is achieved in the apparatus 1800, for example, by switching the microprocessor off (either in complete power down mode or in a sleep mode) between collection sessions. The clock 1814 provides an on/off signal to a power switch 1816. The power switch is operatively coupled to the clock 1814 and the processor 1806.

The apparatus 1800 may additionally include a power capacitor 1818. The power capacitor 1818 is operatively coupled to the power supply to minimize high current draw spikes that normally occur during the power on cycle of a microprocessor. This has the effect of reducing the effects of power spikes and increasing longevity of the battery.

In normal design using integrated circuits that require power, a filtering capacitor may be inserted between power and ground to filter out any noise that may be induced by the integrated circuit into the power lines. There are also very high power draws on some integrated circuits such as micro-processors during startup. In an example embodiment, the filtering capacitor is advantageously used as a temporary storage for power, so that there is enough power during start up as small power cells (batteries) suitable for compliance measurement devices are not able to supply the current required to startup a CPU. If a power cell is able to supply the current, the startup current spikes may reduce the life span of the battery. The use of the capacitor allows the shut down and power on of the CPU and other components without any issues during the on/off cycle. This significantly increases the longevity of the compliance measurement device.

The power switch 1816 is configured to periodically toggle the processor 1806, memory 1810, temperature sensor 1808, and the spatial orientation sensor 1802 between an off-state and an on-state based on the on/off signal provided by the clock 1814. The processor 1806 is configured to control the temperature sensor 1708 and the spatial orientation sensor 1712 during the on-state.

Power is turned on, for example, once a minute by the on/off signal from the real-time clock 1814. The microprocessor 1806 may read operational information contained in the real-time clock and execute the functions associated with a session. At the end of the session the microprocessor may verify if the apparatus 1800 is docked (wired or wireless) to a base-station (not shown) and whether the base station is trying to communicate with it, for example, via the communication module 1802. If so a communication session is performed to transfer data to/from the memory 1810. If the apparatus 1800 is not docked to the base station or at the end of the communication session, the microprocessor power may be powered off (completely or to a sleep mode). This method has the advantage of significantly reducing power requirements and thus allows the device to last longer while still collecting more adequate signal information.

Figure 19:
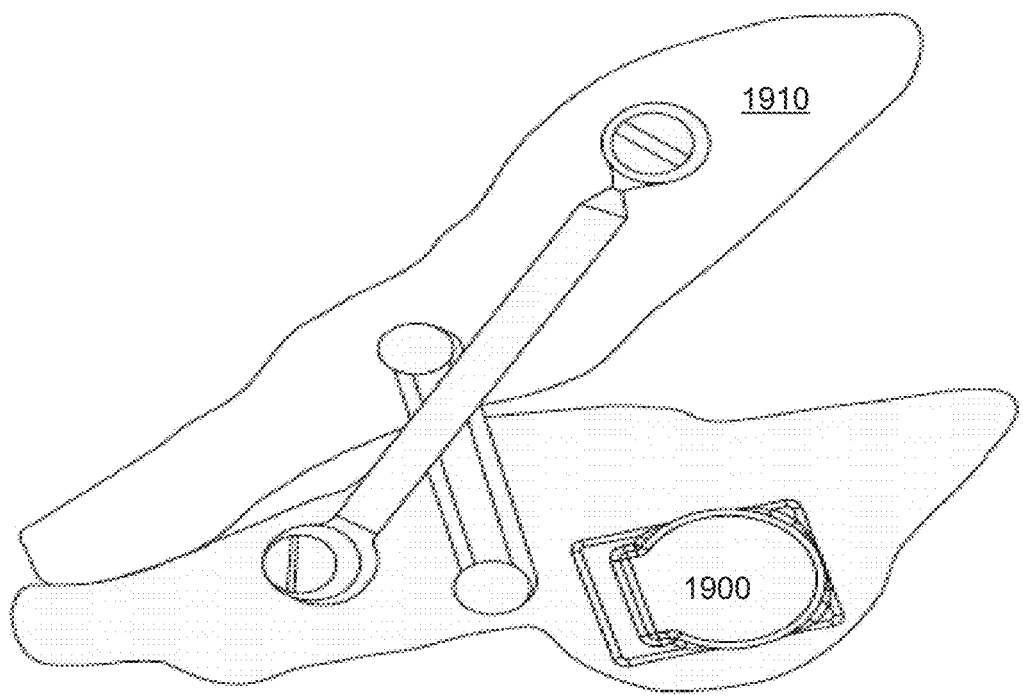
FIG. 19 shows perspective view of a dental appliance fitted with the compliance monitoring apparatus of the present disclosure.

In an example embodiment, the dental appliance therapy compliance monitoring apparatus 1900 can be manufactured to fit easily within a dental appliance 1910 or embedded therein, as shown in FIG. 19.

Figure 20:
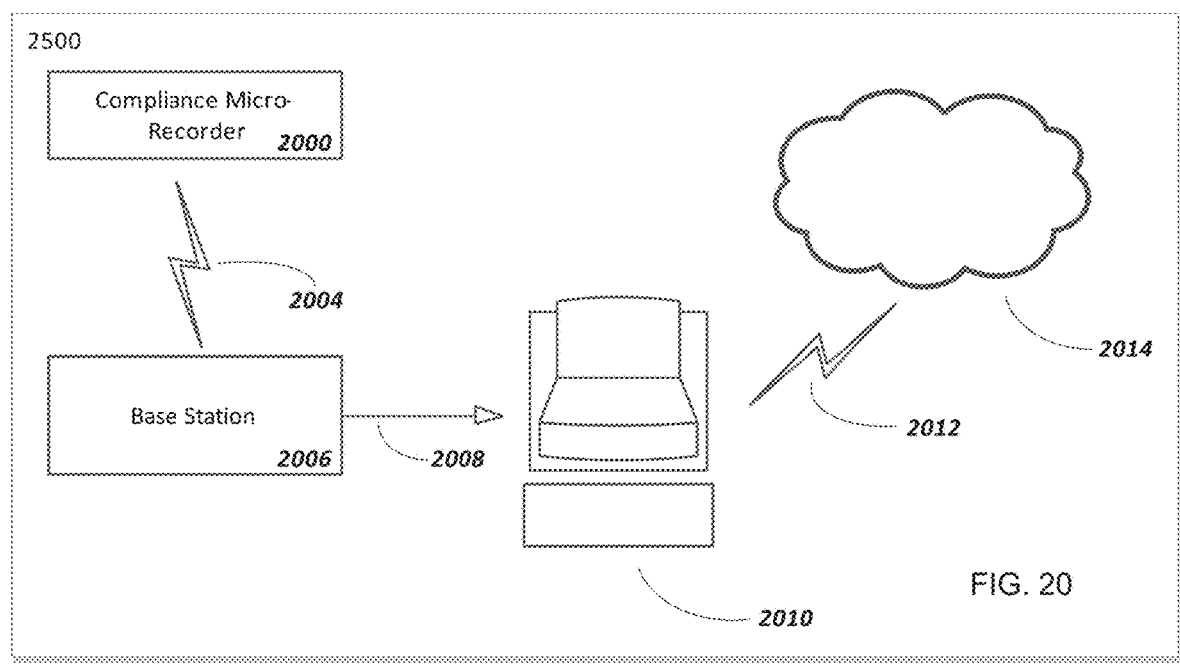
FIG. 20 is a block diagram of a dental appliance therapy compliance verification system in accordance with an aspect of the present disclosure.

FIG. 20 is a block diagram of a dental appliance therapy compliance verification system in accordance with an aspect of the present disclosure. The system 2500 comprises a dental appliance therapy compliance monitoring apparatus (or a compliance micro-recorder) 2000; and an compliance verification processor 2010. The compliance micro-recorder 2000 includes a battery to power the apparatus; a temperature sensor to measure an ambient temperature of the apparatus; a spatial orientation sensor to measure a spatial orientation of the apparatus; a processor configured to control the temperature sensor and the spatial orientation sensor to periodically measure the ambient temperature and the spatial orientation to obtain a time-domain series of ambient temperature measurements and a time-domain series of spatial orientation measurements, respectively; a memory operatively coupled to the processor to record the ambient temperature measurements and the spatial orientation measurements; and a communication module operatively coupled to the processor. The compliance verification processor 2010 is configured to communicate with the communication module of the compliance micro-recorder 2000 via a base station 2006 over communication links 2004 and 2008 (wired or wireless) to communicate the recorded time-domain series of ambient temperature measurements and the time-domain series of spatial orientation measurements and to determine compliance with the dental appliance therapy.

The compliance micro-recorder 2000 may be embedded within an oral appliance. The compliance micro-recorder 2000 is docked with the base station 2006 via a communication link 2004. Communication between the base station 2006 and the compliance micro-recorder is done wirelessly by optical or electromagnetic means. The base station 2006 is connected to a computer 2010 through a USB or other similar computer interface module (or via suitable wireless protocols). The computer 2010 may connected to the internet where communication via link 2012 to a cloud application 2014 where data or other appliance and/or patient-related information may be stored. Further analysis of the data can be done at any location with this setup.

Generally, the apparatus and system of the present disclosure uses a temperature sensor such as a thermistor for collecting temperature and a spatial orientation sensor such as an accelerometer for collecting head position and head movement. In example embodiments, the CPU samples at 1 minute intervals. Data is stored once every 5 to 15 minutes depending on what the user/dental practitioner desires. Data storage consists of the temperature at the time the data was stored, with 0.1° C. accuracy, a delta temperature that is the range of temperature variation since the last time data was stored, head position at the time the data was stored and a measure of head movement which is the range of acceleration measurements since the last time data was stored. This information is analyzed using spectral analysis for any periodic frequencies that could be used to indicate that the oral appliance is in an artificial environment. This information coupled with a minimum temperature and over temperature and head position can be used to increase the accuracy on reporting if the device is being worn.

Similarly spectral analysis for the movement of the head and change in head position can be used to indicate if the device is in the mouth of the patient or not. It may be possible to further increase accuracy by using the head position and head movement to indicate the probability that the patient was asleep while wearing the device.

Certain aspects of the methods described herein may be provided in a tangible computer-readable medium having recorded thereon non-transitory instructions, which when executed by a processor causes a computer to perform a method for verifying compliance with a dental appliance therapy for a human patient as described herein.

While the invention has been described in terms of exemplary embodiments, those skilled in the art will recognize that the invention can be practiced with modification within the scope of the appended claims. The included examples are merely illustrative and are not meant to provide an exhaustive list of possible embodiments and applications. Additionally, it should be understood that while the present invention is presented in the scope of a mandibular advancement device for the treatment of sleep apnea, the present method may equally be applied to other fields, such as dental and orthodontic corrective devices.

What is claimed is:

1. A dental appliance therapy compliance system comprising:
   a compliance monitoring apparatus for use with a dental appliance; and
   a compliance verification apparatus coupled for communication with the compliance monitoring apparatus over a communication link,
   the compliance monitoring apparatus comprising:
      a spatial orientation sensor operable to measure a spatial orientation of the apparatus relative to a direction of gravity;
      a compliance monitoring processor operatively coupled to the spatial orientation sensor and operable to generate a series of maximum spatial orientation variation magnitudes corresponding respectively to a series of periods during a dental appliance therapy session, wherein for each of the periods, the compliance monitoring processor is operable:
         to use the spatial orientation sensor to generate a plurality of spatial orientation measurements corresponding respectively to a series of intervals within the period;
         to determine a magnitude of a maximum variation of the plurality of spatial orientation measurements, to generate the maximum spatial orientation variation magnitude corresponding to the period;
      a compliance monitoring memory operatively coupled to the compliance monitoring processor to store the series of maximum spatial orientation variation magnitudes;
      a battery operatively coupled to power the spatial orientation sensor, the compliance monitoring processor, and the compliance monitoring memory; and
      a communication module operatively coupled to the compliance monitoring processor to communicate the stored series of maximum spatial orientation variation magnitudes to the compliance verification apparatus; and
   the compliance verification apparatus comprising a compliance verification processor operable to perform a method for verifying compliance with the dental appliance therapy for a human patient by determining whether the dental appliance was in a human mouth during the dental appliance therapy session or was in a water bath during the dental appliance therapy session, the method comprising:
      receiving at the compliance verification processor from the compliance monitoring apparatus over the communication link the series of maximum spatial orientation variation magnitudes;
      transforming by the compliance verification processor at least a portion of the series of the maximum spatial orientation variation magnitudes to a frequency-domain series of maximum spatial orientation variation magnitudes;
      determining by the compliance verification processor a spatial orientation power ratio of a total power in each of two frequency bands in the frequency-domain series of maximum spatial orientation variation magnitudes, the two frequency bands including a first frequency band indicative of a physiological spatial orientation frequency characteristic of a human mouth and a second frequency band indicative of a mechanical spatial orientation frequency characteristic of a water bath;
      determining by the compliance verification processor that the dental appliance was in the human mouth during the dental appliance therapy session when the spatial orientation power ratio is within pre-selected power ratio tolerances, and otherwise determining that the dental appliance was in the water bath; and, transmitting or storing data related to the determined compliance.

2. A dental appliance therapy compliance monitoring apparatus for use with a dental appliance during a dental appliance therapy session, the apparatus comprising:
   a spatial orientation sensor operable to measure a spatial orientation of the apparatus relative to a direction of gravity;
   a processor operatively coupled to the spatial orientation sensor and operable to generate a series of maximum spatial orientation variation measurements corresponding respectively to a series of periods during the dental appliance therapy session, wherein for each of the periods, the processor is operable:
  to use the spatial orientation sensor to generate a plurality of spatial orientation measurements corresponding respectively to a series of intervals during the period;
  to determine a magnitude of a maximum variation of the plurality of spatial orientation measurements, to generate a maximum spatial orientation variation magnitude corresponding to the period,
wherein, for each of the periods, the corresponding maximum spatial orientation variation measurement comprises the maximum spatial orientation variation magnitude;
  a memory operatively coupled to the processor to store the series of maximum spatial orientation variation measurements;
  a battery operatively coupled to power the spatial orientation sensor, the processor, and the memory; and
  a communication module operatively coupled to the processor to communicate the stored series of maximum spatial orientation variation measurements.

3. The apparatus according to claim 2, wherein:
for each of the periods, one of the spatial orientation measurements is a base spatial orientation measurement; and
the processor is operable to determine the maximum spatial orientation variation magnitude by determining a magnitude of an absolute maximum of differences between: the base spatial orientation measurement; and, each of the other spatial orientation measurements.

4. The apparatus according to claim 3, wherein, for each of the periods, the base spatial orientation measurement is the spatial orientation measurement corresponding to a first interval of the series of intervals.

5. The apparatus according to claim 4, wherein each interval is one minute, each period is five minutes, and the processor is operable:
  to use the spatial orientation sensor to generate the base spatial orientation measurement corresponding to the first interval;
  to use the spatial orientation sensor to generate the other spatial orientation measurements corresponding to second, third, fourth, and fifth intervals of the series of intervals; and
  to store the base spatial orientation measurement and the maximum spatial orientation variation magnitude as the maximum spatial orientation variation measurement corresponding to the period.

6. The apparatus according to claim 5, wherein the processor is operable to generate and store in the memory the maximum spatial orientation variation measurement without storing in the memory any of the other spatial orientation measurements.

7. The apparatus according to claim 3, wherein, for each of the periods, the corresponding maximum spatial orientation variation measurement further comprises the base spatial orientation measurement.

8. The apparatus according to claim 2, wherein:
each spatial orientation measurement comprises a gravity vector representing the direction of gravity relative to the spatial orientation of the dental appliance; and
the processor is operable to determine the magnitude of the maximum variation of the plurality of spatial orientation measurements by determining a maximum vector difference of the plurality spatial orientation measurements, and computing a magnitude of the maximum vector difference.

9. The apparatus according to claim 2, wherein:
each spatial orientation measurement comprises a gravity vector representing the direction of gravity relative to the spatial orientation of the dental appliance; and
the processor is operable to determine the magnitude of the maximum variation of the plurality of spatial orientation measurements by determining a maximum vector difference of the plurality spatial orientation measurements in two dimensions of the gravity vector.

10. The apparatus according to claim 2, wherein:
the processor is operable to determine the maximum spatial orientation variation magnitude by determining a magnitude of an absolute maximum of differences between consecutive spatial orientation measurements.

11. The apparatus according to claim 2, wherein the spatial orientation sensor is a three-axis accelerometer.

12. The apparatus according to claim 2, wherein each interval is one minute, and each period is five minutes.

13. The apparatus according to claim 2, wherein the processor is operable to store in the memory the maximum spatial orientation variation measurement for each period at or after an end of the period.

14. The apparatus according to claim 2, wherein:
the apparatus further comprises a temperature sensor operable to measure an ambient temperature of the apparatus;
the processor is further operatively coupled to the temperature sensor and operable to use the temperature sensor to generate a series of ambient temperature measurements;
the memory is further operatively coupled to the processor to store the series of ambient temperature measurements;
the battery is further operatively coupled to power the temperature sensor; and
the communication module is further operatively coupled to the processor to communicate the stored series of ambient temperature measurements.

15. The apparatus according to claim 14, wherein the temperature sensor is a thermistor.

16. The apparatus according to claim 2, further comprising:
a clock operable to provide an on/off signal to a power switch, the power switch being operatively coupled to the battery, the clock and the processor and operable to periodically toggle the processor between an on-state and an off-state responsive to the on/off signal, wherein the battery is operatively coupled to power the clock; and
wherein the processor operable to use the spatial orientation sensor during the on-state.

17. The apparatus of claim 16, wherein in the off-state the processor is unpowered.

18. The apparatus of claim 16, wherein the power switch toggles to turn on power to the processor at intervals of one minute.

19. The apparatus of claim 16, wherein the spatial orientation sensor is powered during the on-state for less than one millisecond, and is unpowered in the off-state.

20. A processor for a dental appliance therapy compliance monitoring apparatus for use with a dental appliance during a dental appliance therapy session, the apparatus comprising:
  a spatial orientation sensor operable to measure a spatial orientation of the apparatus relative to a direction of gravity;

a memory to store a series of maximum spatial orientation variation measurements; and a communication module to communicate the stored series of maximum spatial orientation variation measurements, wherein the processor is configured for operative coupling to the spatial orientation sensor, the memory, and the communication module, and is operable:

to generate a series of maximum spatial orientation variation measurements corresponding respectively to a series of periods during the dental appliance therapy session, wherein for each of the periods, the processor is operable:

to use the spatial orientation sensor to generate a plurality of spatial orientation measurements corresponding respectively to a series of intervals within the period;

to determine a magnitude of a maximum variation of the plurality of spatial orientation measurements, to generate a maximum spatial orientation variation magnitude corresponding to the period, wherein, for each of the periods, the corresponding maximum spatial orientation variation measurement comprises the maximum spatial orientation variation magnitude;

to store the series of maximum spatial orientation variation measurements in the memory; and to control the communication module to communicate the stored series of maximum spatial orientation variation measurements.

\* \* \* \* \*